United States Patent [19]
Boydle et al.

[11] Patent Number: 5,567,888
[45] Date of Patent: Oct. 22, 1996

[54] SAMPLING DEVICE

[76] Inventors: Timothy Boydle, c/o Lintec Marketing 6 Headland Road, Castle Cove, New South Wales 2069; Patrick O'Brien, Blink Bonie Lodge, Wirrinya, New South Wales 2781, both of Australia

[21] Appl. No.: 365,600

[22] Filed: Dec. 27, 1994

[30] Foreign Application Priority Data

Dec. 24, 1993 [AU] Australia ................................. PM3154
Jun. 16, 1994 [AU] Australia ................................. PM6252

[51] Int. Cl.⁶ ............................................................ G01N 1/00
[52] U.S. Cl. ......................................................... 73/863.86
[58] Field of Search ........................... 73/863.31, 863.33, 73/863.81, 863.82, 863.83, 863.86, 864.64

[56] References Cited

U.S. PATENT DOCUMENTS

| | | | |
|---|---|---|---|
| 840,943 | 1/1907 | Ingold | 73/863.33 |
| 2,702,475 | 2/1955 | Dougherty et al. | 73/863.33 |
| 4,072,059 | 2/1978 | Hamilton | 73/864.64 |
| 4,616,515 | 10/1986 | Dancoine | 73/863.83 |
| 4,800,765 | 1/1989 | Nelson | 73/864.64 |

FOREIGN PATENT DOCUMENTS 2071846  9/1981  United Kingdom ................ 73/863.86

*Primary Examiner*—Robert Raevis
*Attorney, Agent, or Firm*—McAulay Fisher Nissen Goldberg & Kiel, LLP

[57] ABSTRACT

A device for obtaining samples of stockpiled granular material comprises an elongated tubular member extending into a silo through the base thereof. The tubular member has an array of first holes along a side thereof. An elongated plate with a plurality of second holes is juxtaposed to the side of the tubular member. A manually operable shifting lever is connected to the plate for shifting the plate longitudinally along the tubular member, alternately to align the second holes with the first holes to enable collection of granular samples from the silo via the tubular member and to misalign the first and second holes to prevent entry of granular material into the tubular member. Where the silo has a lid at the top thereof for covering an opening in the top, an additional manual shifter is operatively connected to the lid and to the tubular member for enabling a manual shifting of the lid relative to the top to alternately open and close the opening.

11 Claims, 7 Drawing Sheets

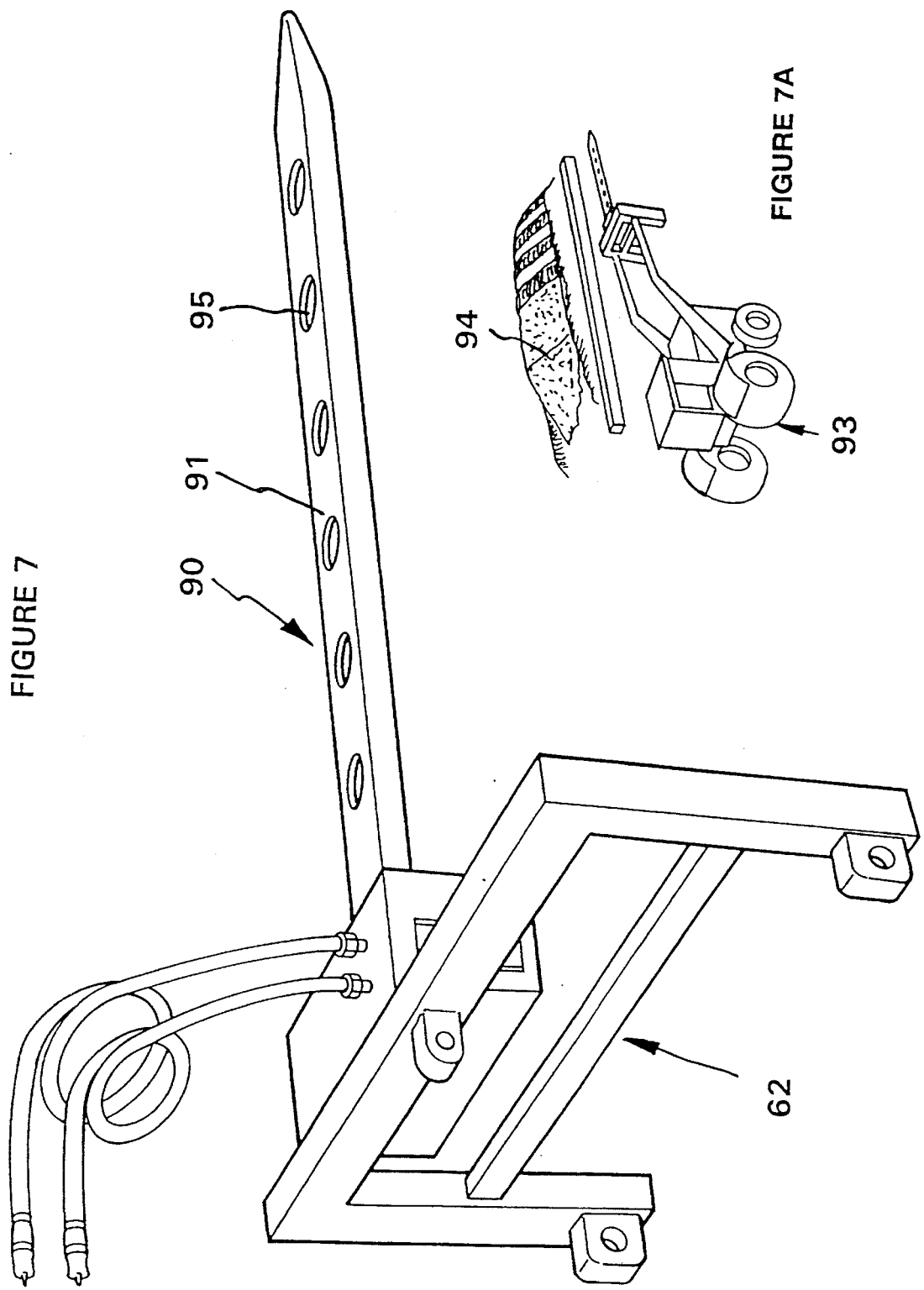

5,567,888

SAMPLING DEVICE

SAMPLING DEVICE

The present invention relates to a sampling device for sampling for the purpose of testing the integrity of free standing material heaps such as grain stockpiles and of the contents of storage receptacles such as grain silos and more particularly, for sampling grain at various depths in the stockpile. The invention may also be adapted to a variety of applications where it is necessary to test the integrity of the contents of granular material particularly where it is difficult to gain access to the inner depths of the material whose integrity must be determined.

It will be understood that the present invention, although suitable for a variety of applications where the integrity of the contents of stockpiles of granular material is to be sampled the invention will be described principally with respect to its application to testing the integrity of grain held in agricultural silos or grain storage receptacles used in grain transportation.

In the agricultural industry it is necessary to continually check the quality and integrity of free standing grain stockpiles and of grain held in various receptacles including silos. Grain is usually held in silos for temporary storage prior to transit to manufacturing and processing plants or for later export.

It is usual practice to take running samples as a silo is filled however, this practice is very often not adhered to so that the quality of grain contained in silos is not always known and for that matter cannot be determined easily. It is very important to continually monitor (by sampling) the protein levels in grain in particular and also to ensure that there is no moisture contamination, weight change, weevil infestation or visual degradation. At the moment it is very difficult to obtain core samples from the material inside the silo or from grain stockpiled in the open or held in transit receptacles. Presently samples from silos are generally taken by gaining access through a lid of the silo and taking a representative sample from the top of the contents. It is possible to take a sample a short depth from the top but this is not necessarily representative of samples which should be taken from the inner depths of the grain heap.

When a purchaser takes delivery of grain he may require evidence such as a grain quality report which indicates the integrity of the grain purchased. The certificates indicate the protein content and other parameters which go to the integrity of the grain purchased all of which have a bearing on the value per tonne of the grain supplied.

It has not previously been possible to obtain in an expedient way an adequate representative sample of grain stored in bulk and in particular a core sample.

The present invention seeks to overcome the inherent problems in obtaining a representative sample of bulk stored material particularly grain by providing a sampling device, either fixed permanently or detachably fixed to a storage container or alternatively, able to penetrate and withdraw from the space in which grain is bulk stored wherein the device enables a representative or average sample of stored material to be obtained simply and easily without breaking the seal in a storage container or alternatively, to enable access to the inner core of bulk stored granular material or grain dumps in the open above the ground or in storage receptacles below the ground. According to the invention, representative samples may be taken from the inside of bulk stored granular material at incremental depths.

The invention in its many applications has a number of attendant advantages including; accurate and efficient sampling, accurate estimation of the parameters of the granular material which go to its integrity, quality control management of grain dumps preservation of price per unit volume, monitoring of moisture levels and vermin degradation including that by rats, mice, weevils, insects and other pests facility for fumigation of the grain and preservation of grain for live stock feeding.

Not only is the device according to the present invention used for testing long term stored grain but it is also useful for checking the integrity of grain at the point of delivery and either prior to or immediately upon transfer of the grain to a storage facility.

In one broad form, the present invention comprises;

a sampling device for obtaining a representative sample of the stored contents of an open or closed storage container such as a silo, the device comprising;

an elongated hollow member including a through passage communicating between a first end and a second end wherein a portion of the sampling device intermediate said ends engages said contents so that at least one of said ends extends beyond said contents such that its outer surface near the end of the elongated is free of said contents;

at least one opening in at least one wall of the elongated member, actuating means operable from said first end to enable covering and uncovering of said at least one opening, wherein, when said opening/s is/are uncovered the contents of the silo or storage receptacle enter the passage and exit the silo via said free end.

In another form the present invention comprises;

an assembly for testing the integrity of granular material; the assembly comprising;

a mobile gantry and a sampling assembly wherein the sampling assembly includes a sampling device comprising, an elongated member having first and second ends and a hollow interior with a through passage which communicates between the first and second ends; said elongated member including at least one hole which communicates between the outside of said member and the hollow interior; and, means to enable selective opening and closing of said at least on hole, whereupon when the elongated member penetrates or is enveloped by granular material, said material penetrates said at least one hole so that a sample of the material is obtainable from within the elongated member via a free end.

In its broadest form, the present invention comprises:

a device for obtaining a representative sample of stockpiled granular material; the device comprising;

an elongated member having first and second ends and a hollow interior with a through passage which communicates between the first and second ends; said elongated member including at least one hole which communicates between the outside of said member and the hollow interior; and, operating means to enable selective opening and closing of said at least one hole, whereupon when the elongated member penetrates or is enveloped by granular material, said material is able to penetrate said at least one hole, if open, so that a sample of the material is obtainable from within the elongated member via one of the ends.

According to one embodiment the sampling device includes an array of holes spaced apart along the length of the elongated member wherein the holes may be selectively blocked or laid open responsive to actuation of a plate having holes which may either be pierced in alignment with or out of alignment with the holes in the elongated member. The sampling device may be arranged in the form of a probe which is able to penetrate and sample stockpiled grain. Alternatively, the sampling device is located in an open storage bin which may be carried on a vehicle such that the first and second ends of the elongated member are free of the contents.

According to a preferred embodiment the sampling device may be fixed permanently to the silo and also includes when used for testing the contents of a silo an accompanying silo lid opening device operable from remote actuation means at or near the base of the silo conveniently accessible to an operator. The lid opening facility precludes the need for an operator to climb the silo or to personally gain access to the interior for taking the sample. This increases the safety aspects of obtaining such representative samples as the operator does not need to climb to the top of the silo.

The present invention will now be described in more detail according to a preferred but non-limiting embodiment and with reference to the accompanying illustrations wherein;

FIGS. 7, 7A shows a sampling device in the nature of a probe which may be detachably fixed to a vehicle for penetrating grain heaps for lateral sampling and withdrawal.

Figure 1:
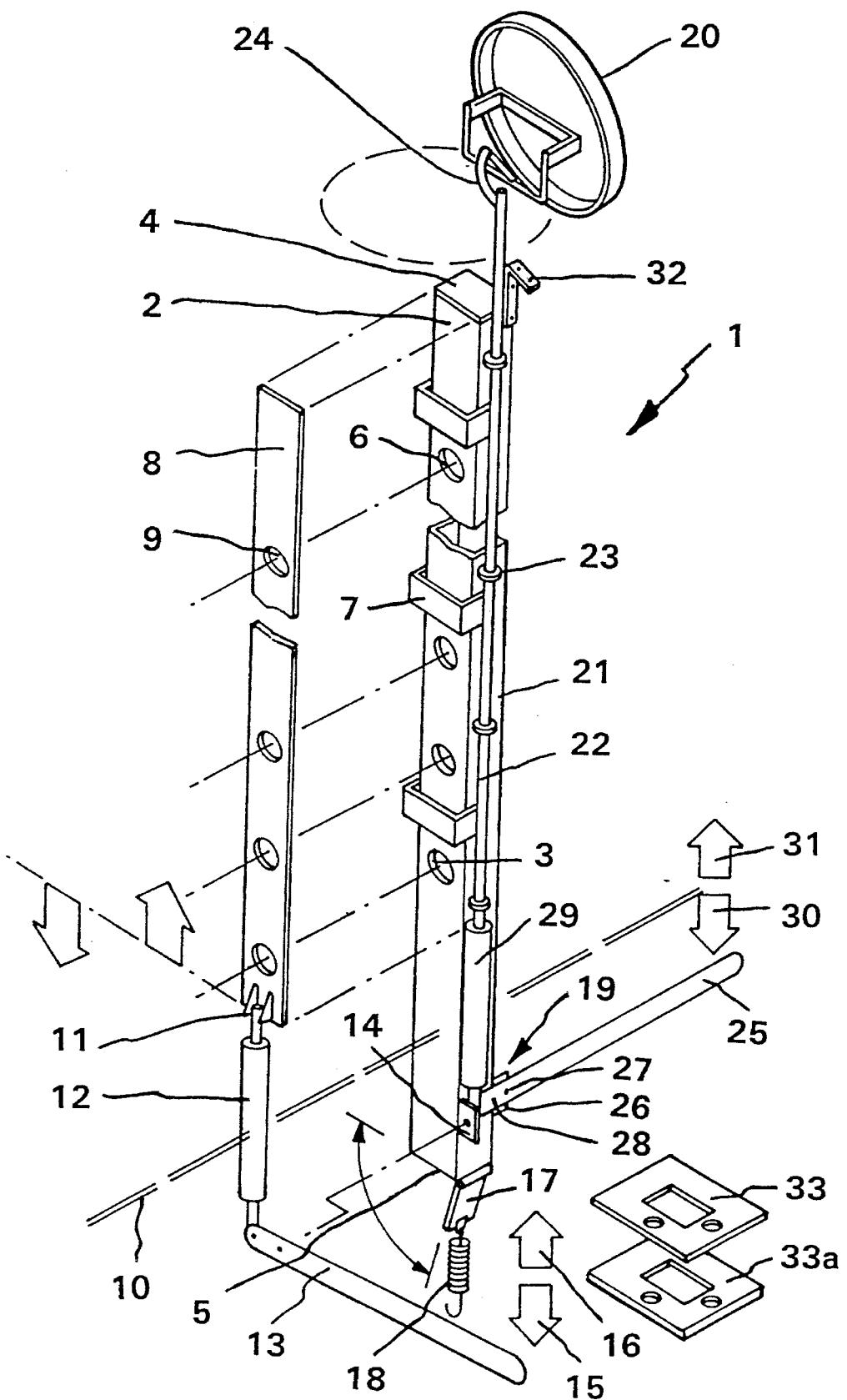
FIG. 1 shows an exploded view of a sampling device according to a preferred embodiment of the invention.

Referring to FIG. 1 there is shown an exploded view of a sampling device 1 according to a preferred embodiment of the invention. The device comprises elongated grain collection tube 2 having a through passage 3 which communicates between ends 4 and 5. The grain collection tube 2 preferably spans from outside the base of the silo to just inside the silo lid 20. Collection tube 2 includes one or more openings 6 which allow ingress of grain into passage 3 when sampling is to take place. Collection tube 2 includes guide members 7 between which travels moveable gate 8. Gate 8 includes at least one opening 9 which, depending on its position relative to collection tube 2, aligns or misaligns with openings 6 in the collection tube 2. When device 1 is fixed to a grain storage silo, end 5 of the elongated tube 2 extends beyond the silo floor indicated by line 10. Gate 8 terminates at end 11 in a sealing element 12 which locates partially within the storage silo and partially outside. Sealing member 12 terminates at handle 13 which regulates the travel of gate 8 between guides 7 and collection tube 2. When gate 8 is in position, between collection tube 2 and guides 7, handle 13 which connects to a tab 14 on collection tube 2 provides a fulcrum about which handle 13 pivots in order to operate gate 8. Gate 8 travels in the direction of the longitudinal axis of the collection tube 2 such that it moves between a location where holes 9 and 6 may be aligned and where those holes are out of alignment. The open or aligned relationship between plate 8 and elongated member 2 in the aligned or open configuration is indicated by arrow 15. Arrow 16 indicates the direction plate 8 travels in order to misalign corresponding holes 9 and 6. According to an alternative embodiment these roles may be reversed. At end 5 of the collection tube 2 there is a hinged lid 17 which enables a through passage 3 to be accessed or closed off. Lid 17 includes tension spring 18 which ensures that lid 17 is subjected to positive pressure to ensure proper resealing.

In use, when a sample of the internal contents of grain stored in a vessel such as a silo is required, the operator opens lid 17 which will allow granular material which enters through passage 3 to fall into a sampling receptacle provided by an operator. In order to obtain the sample the operator activates handle 13 which pivots about a pin connection in tab 14. When handle 13 is actuated, plate 8 moves so that holes 9 and 6 and any corresponding holes which appear in the plate 8 and collection tube 2 respectively are in alignment. Once they are in alignment, grain from the silo gravitates through the holes into the through passage 3 and then gravitates into the collection receptacle as the granular material exits via end 5 of the collection tube 2.

According to a preferred embodiment, the device 1 also includes a lid operating assembly 19 which engages lid 20 and enables an operator remote from the lid to open and close it according to requirements. According to the embodiment of FIG. 1, the attachment is affixed to face 21 of tube 2 and comprises elongated rod 22 which is anchored to surface 21 via saddles 23, Rod 22 includes at one end operating member 24 which engages lid 20 in order to effect opening and closing upon actuation of actuating handle 25. Actuating handle 25 is anchored to collection tube 2 via tab 26 and pivots about pivot pin 27. End 28 of handle 25 engages sealing member 29 which is similar to sealing member 12. Preferably, saddles 23 allow loose fitting of red so that it can freely move axially.

The lid operating assembly 19 allows for ground level personnel to open the silo lid remotely when grain filling, fumigating or obtaining a core sample, This provides a safety mechanism and reduces or eliminates the need to climb the silo or indeed to enter it. Lid 20 is opened by operating lever 25 when the lever is moved in the direction of arrow 30. In order to close lid 20, lever 25 is moved in the direction of arrow 11. Fumigation of the contents of a storage vessel can be effected via lid 17 wherein a cylinder containing the fumigation gas is introduced at end 5 so that the gas is able to enter through passage 3 and once holes 9 and 6 are aligned, the gas can then permeate through the granular contents of the silo or storage receptacle. End 4 of sampling device 1 is fitted to a silo via connecting bracket 32 and this can be connected preferably by bolting. The bottom end of the sampling device is fitted to a floor wall of the storage receptacle via anchor plates 33 and 33a, one of which is bolted to the inside of the wall and the other to the outside of the wall.

Preferably, the sampling device is manufactured from steel however, it will be appreciated that a number of different types of materials can be used for construction of the sampling device including plastics and timber.

Figure 2:
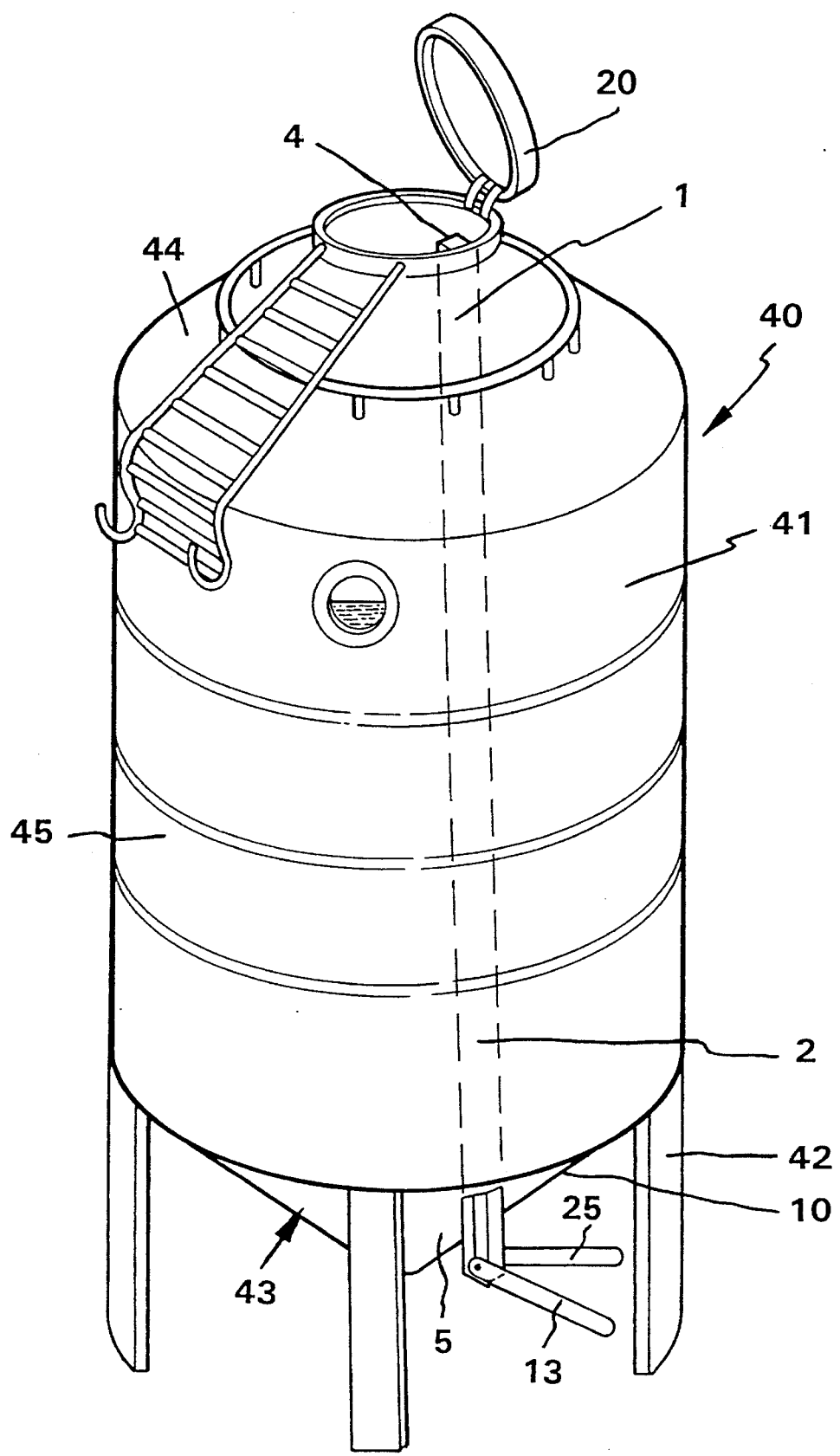
FIG. 2 shows an isometric view of an elevated grain storage silo similar to that shown in FIG. 2 indicating the preferred attitude of the sampling device.

FIG. 2 shows an isometric view of a silo 40 including the sampling device 1 of FIG. 1 in situ.

The silo shown comprises storage receptacle 41 mounted on support stand 42. Typically silos of this type have a pyramidal base 43 and top 44. The silo includes lid 20 which enables access to be gained to the sapling device and also to the contents of the silo. Sampling device 1 comprises ends 4 and 5 wherein end 4 terminates inside the storage receptacle 41 and end 5 terminates outside silo floor 10 which forms part of the base 43 of receptacle 41. End 4 includes means to enable remote opening of lid 20 (see description for FIG. 1). End 5 includes a hinged lid 17 which may be opened to allow release of contents 45 from the through passage 3. Preferably sampling device 1 is anchored to receptacle 41 by means of anchor plates 33 and 33a with plate 33 engaging inner surface and plate 33a engaging outer surface of receptacle 41. In use when an operator requires a sample of the contents 45 of the receptacle 41 he operates a lever at the end 5 of the sampling device (see FIG. 1) which allows the contents 45 of the receptacle 41 to gravitate through openings in the device into through passage 3 whereupon the contents gravitate to the exterior of the receptacle via end 5.

FIG. 2 shows a schematic arrangement of a sampling device inside an above ground silo.

Figure 3:
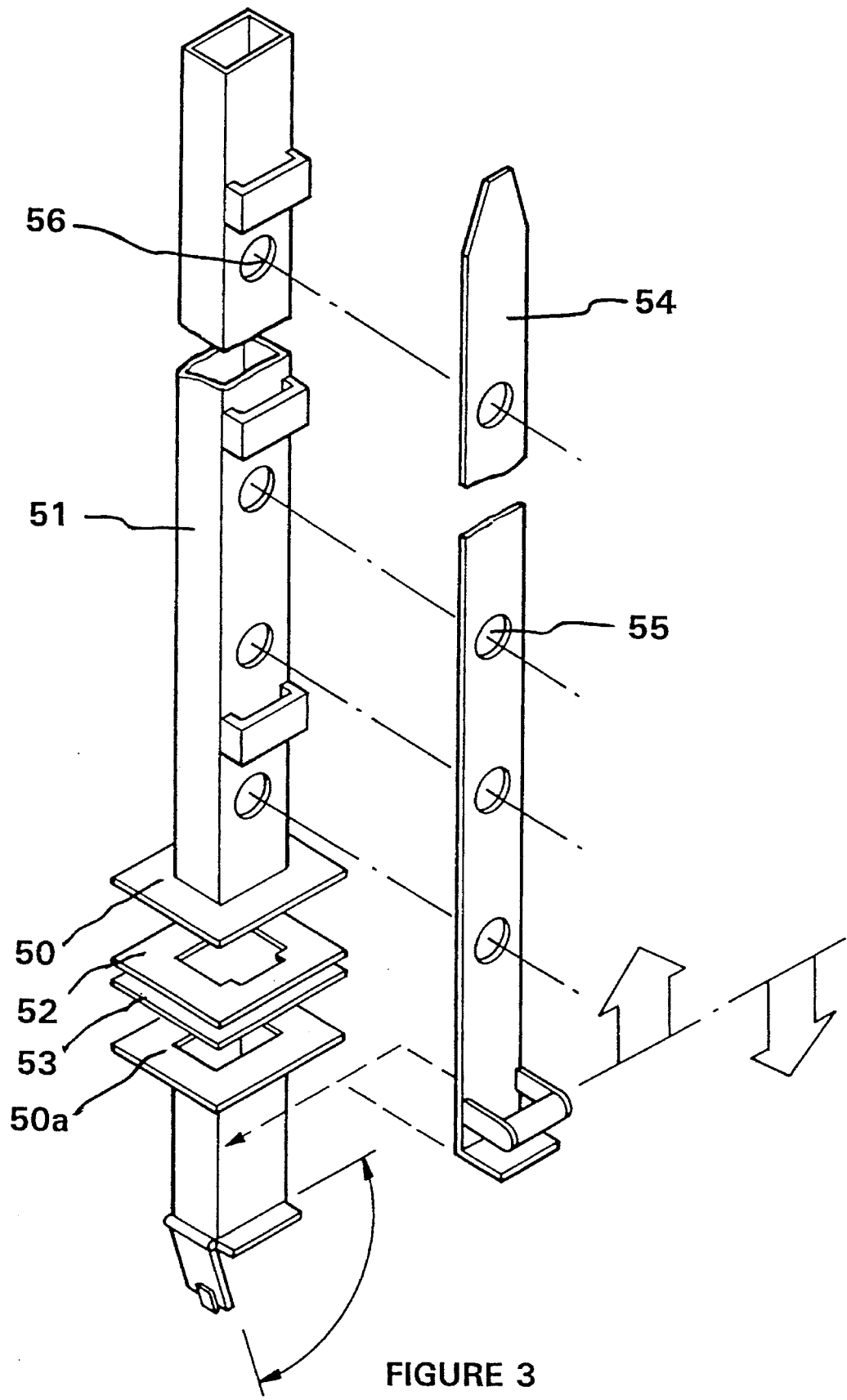
FIG. 3 shows an exploded view of a sampling device according to an alternative embodiment of the invention.

FIG. 3 shows a exploded view of a sampling device according to an alternative embodiment of the invention. According to this embodiment plates 50 and 50a which correspond to plates 33 and 33a of the embodiment shown in FIG. 1 are welded to sampling tube 32. In order to fit elongated tube 51 to the receptacle it is necessary to drill a hole in the bottom wall of the receptacle to enable clear passage through the sampling tube. When plate 50 is attached to the bottom wall of the receptacle gusset 52 is inserted therebetween to effect a suitable seal. Likewise, gusset 53 is inserted between the outside of the receptacle wall and plate 50a.

Although the sampling device has been described in detail with reference to its application for enabling sampling of grain in a storage receptacle such as a silo, it will be appreciated that the invention can be applied in many different circumstances where sampling of built stored material is required.

Figures 4, 4A:
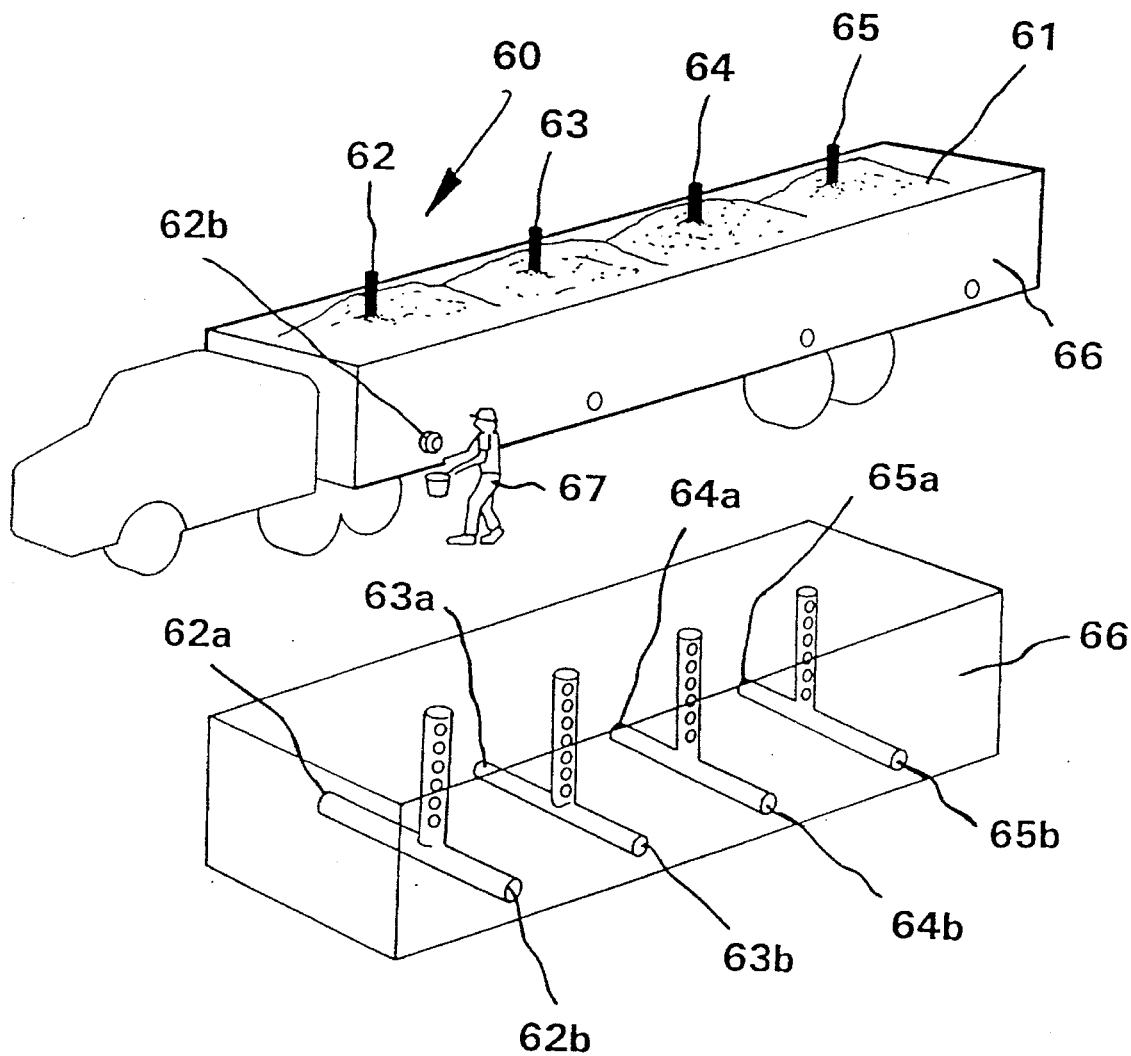
FIGS. 4, 4A shows a sampling device according to one embodiment located in the payload receptacle of a transport vehicle.

FIG. 4 shows an alternative application of the present invention this time using a sampling device in testing the integrity of bulk stored grain in a semi trailer.

According to FIG. 4 there is shown a semi trailer 60 which includes a load of granular material 61 in which is placed a series of collection tubes 62, 63, 64 and 65. FIG. 4 also shows trailer 56 exploded from semi trailer 60 with the grain removed so that the disposition and configuration of the testing devices 62, 63, 64 and 65 can be seen. According to this embodiment each sampling device has outlets free of the granular material 61 and trailer 66. Collection devices 62, 63, 64 and 65, may include outlets on either side of the trailer 66 respectively outlets 62a, 62b, 63a, 63b, 64a, 64b, 65a and 65b. As can be seen in FIG. 4 operator 67 is able to take a sample of the contents of trailer 66 via opening 62b in order to gain an assessment of the integrity of the grain inside the trailer. This is most useful for testing the contents prior to delivery of same.

Figure 5:
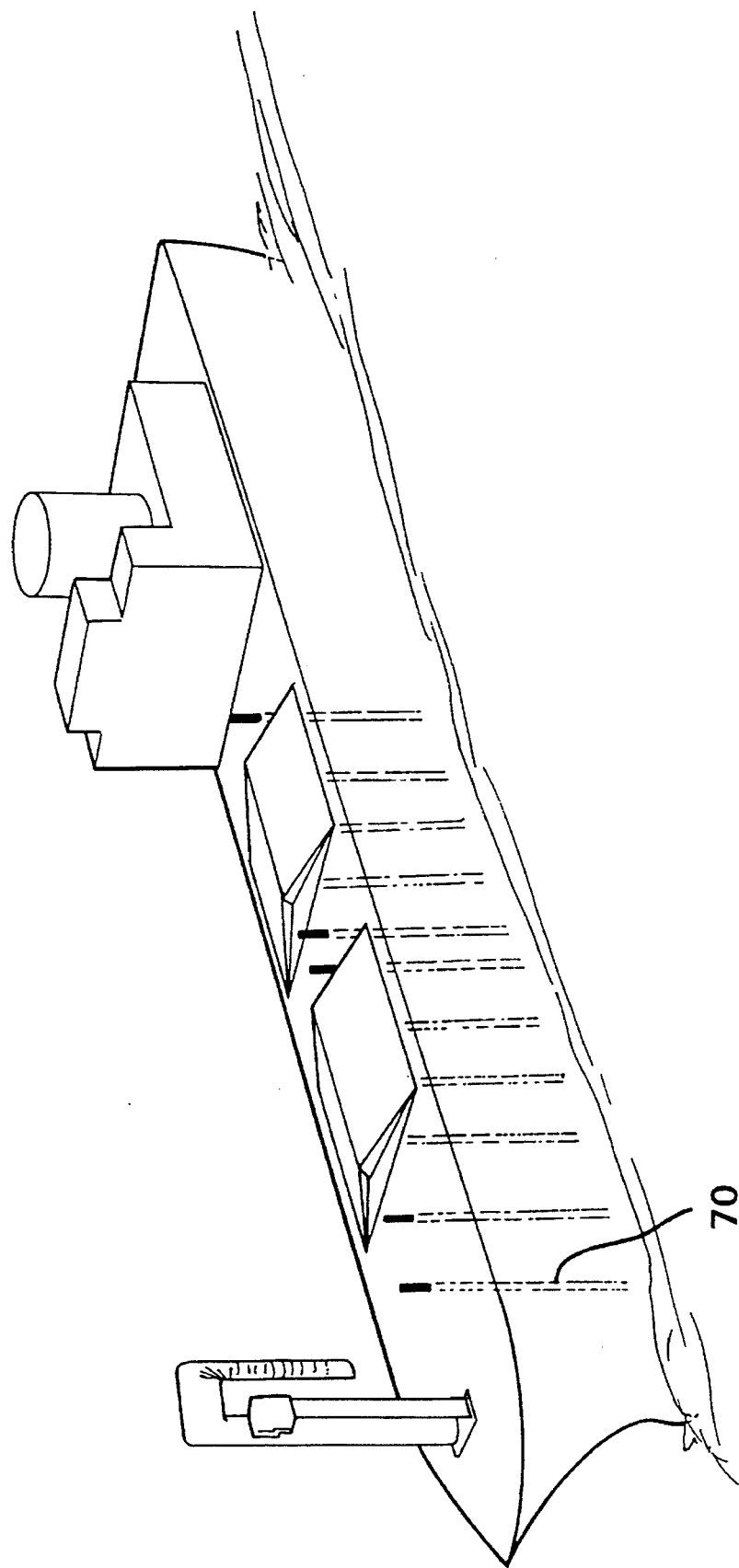
FIG. 5 shows a sampling device according to an alternative embodiment located in a bulk carrier.

FIG. 5 shows an alternative application of the sampling device this time in use for obtaining samples of grain stored in a bulk carrier. According to this embodiment the sampling devices 70 may either be lowered to penetrate the inside portion of the grain or alternatively, they may be adapted with an outlet so the contents under test may gravitate and exit the through passage of the sampling device via an outlet (not shown).

As can be seen in FIG. 5 the sampling devices may be located in the bulk load after loading.

Thus, the sampling device may be used as a probe in field bins which are either fixed or mobile, catching bins and temporary farm storage containers such as a tiger cage or mesh bins.

Figures 6, 6A:
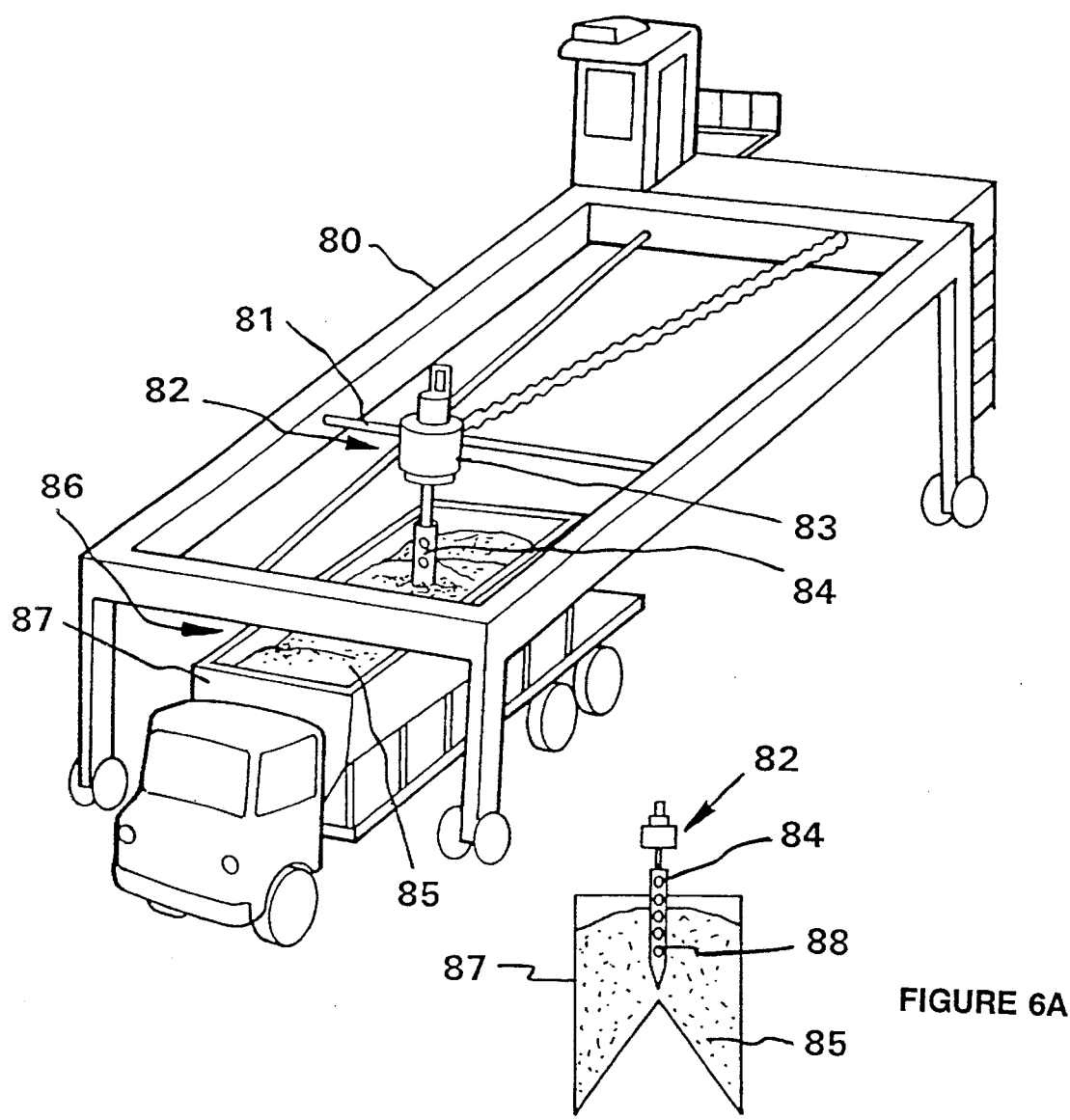
FIGS. 6, 6A shows a mobile support structure including a sampling assembly which acts as a probe which may penetrate and withdraw from a stockpile.

FIG. 6 shows an alternative use for the invention in a fifty automatic control station probe. According to this application a probe which is fixed to a mobile structure is able to be inserted and withdrawn from bulk storage of material contained in a vehicle such as a semi trailer.

Referring to FIG. 6 there is shown mobile support structure 80 which includes a support structure 81 for holding a moveable grain probe assembly 82.

The assembly comprises a drive means 83 to which is attached sampling probe or collection tube 84. Probe 84 is shown inserted into a load of granular material 85 contained in truck 86.

The inset shows a profile of the receptacle of bin 87 of truck 86 with probe assembly 82 inserted therein. From this view the penetration of the collection tube 84 for obtaining a sample into grain 85 can be seen. Sampling device 84 penetrates the grain 85 following which grain enters a through passage in the sampling device 34 via an array of holes 88. It will be appreciated that structure 80 can be moved to a sampling location or alternatively, a vehicle can be backed under the structure as shown enabling the sampling assembly to sample the contents of the vehicle.

Thus, there are a number of ways of applying the invention for obtaining representative samples of bulk stored material, The first is to install a sampling device within a storage receptacle such as a silo wherein the sampling device is fixed in position permanently and where samples can be obtained at any time.

Alternatively, a collecting tube which is anchored to a sampling assembly may be inserted from the top or from the side of a bulk storage of foodstuff such as grain whereupon the probe is withdrawn after the sample has entered holes in the collecting tube. The sample taken can then be tested. Thus, for sapling from bulk storage an implement can be attached to a vehicle such as a tractor.

An example of this is shown in FIG. 7 wherein an attachment 90 includes sampling probe or collecting tube 91 and attachment assembly 92 for attachment to vehicle 93 (see inset in FIG. 7). When the sampling attachment 90 is connected to vehicle 93, the vehicle is simply driven at the grain dump 94 with the probe 91 disposed substantially horizontally wherein the vehicle is driven at the grain dump allowing penetration of probe 91 to the inside of the dump whereupon grain gravitates into collection tube 91 via openings 95.

According to a further application, the device of FIG. 1 may be installed in a mobile silo which for instance is incorporated in railway rolling stock.

It will be recognised by persons skilled in the art that numerous variations and modifications can be made to the invention as broadly described herein without departing from the overall spirit and scope of the invention.

We claim:

1. A storage container with a device for obtaining a sample of stockpiled granular material, comprising:

a silo having a base and a top;

an elongated tubular member extending through said base and into said silo, said tubular member being provided with an array of interspaced first holes along at least one side of said tubular member, said tubular member being mounted to said silo at said base and proximately to said top;

an elongated plate with a plurality of interspaced second holes, said elongate plate being juxtaposed to said one side of said tubular member; and manually operable shifting means operatively connected to said plate for manually shifting said plate longitudinally along said one side of said tubular member alternately to place said second holes in alignment with respective ones of said first holes to enable collection of granular samples via said tubular member from said silo and to displace said first holes relative to said second holes to prevent entry of granular material into said tubular member from said silo, said shifting means essentially comprising a mechanical lever linkage including a moving part extending through said base and further including a manually operable lever pivoting about an anchorage, said lever being pivotably connected to said moving part and located outside said silo wherein said silo is provided at said top with a lid for covering an opening in said top, further comprising additional shifting means operatively connected to said lid and to said tubular member for enabling a manual shifting of said lid relative to said top to alternately open and close said opening.

2. The container according to claim 1 wherein said second shifting means includes a handle disposed at a lower end of said tubular member, outside said silo.

3. The container according to claim 2 wherein said second shifting means further includes a rod extending along said tubular member from said handle to said lid.

4. The container according to claim 1 wherein said tubular member is provided at a lower end with a substantially horizontal extension.

5. A storage container with a device for obtaining a sample of stockpiled granular material, comprising:

a silo having a base and a top;

an elongated tubular member extending substantially vertically through said base and into said silo, said tubular member being provided with an array of interspaced first holes along at least one side of said tubular member, said tubular member being mounted to said silo at a plurality of spaced locations along said silo;

an elongated plate with a plurality of interspaced second holes, said elongated plate being juxtaposed to said one side of said tubular member; and shifting means operatively connected to said plate for manually shifting said plate longitudinally along said one side of said tubular member alternately to place said second holes in alignment with respective ones of said first holes to enable collection of granular samples via said tubular member from said silo and to displace said first holes relative to said second holes to prevent entry of granular material into said tubular member from said silo, said shifting means essentially comprising a mechanical lever linkage with a lever handle extending substantially horizontally at a lower end of said tubular member and wherein said silo is provided at said top with a lid for covering an opening in said top, further comprising additional shifting means operatively connected to said lid and to said tubular member for enabling a manual shifting of said lid relative to said top to alternately open and close said opening.

6. The container according to claim 5 wherein said additional shifting means includes a handle disposed at a lower end of said tubular member, outside said silo.

7. The container according to claim 6 wherein said additional shifting means further includes a rod extending along said tubular member from said handle to said lid.

8. The container according to claim 5 wherein said tubular member is provided at a lower end with a substantially horizontal extension.

9. A storage container with a device for obtaining a sample of stockpiled granular material, comprising:

a silo having a base wall and a top wall, said top wall being provided with an opening covered by a lid;

an elongated tubular member extending through said base and into said silo, said tubular member being provided with an array of interspaced first holes along at least one side of said tubular member, said tubular member being mounted to said silo at least at said base;

an elongated plate with a plurality of interspaced second holes, said elongate plate being movably mounted to said tubular member and juxtaposed to said one side of said tubular member;

first shifting means operatively connected to said plate for manually shifting said plate longitudinally along said one side of said tubular member alternately to place said second holes in alignment with respective ones of said first holes to enable collection of granular samples via said tubular member from said silo and to displace said first holes relative to said second holes to prevent entry of granular material into said tubular member from said silo; and second shifting means operatively connected to said lid and to said tubular member for enabling a manual shifting of said lid relative to said top wall to alternately open and close said opening.

10. The container according to claim 9 wherein said second shifting means includes a handle disposed at a lower end of said tubular member, outside said silo.

11. The container according to claim 10 wherein said second shifting means further includes a rod extending along said tubular member from said handle to said lid.

* * * * *